Aug. 19, 1952 P. SHAMBURGER Plant Pat. 1,121
ROSE PLANT
Filed Feb. 19, 1951
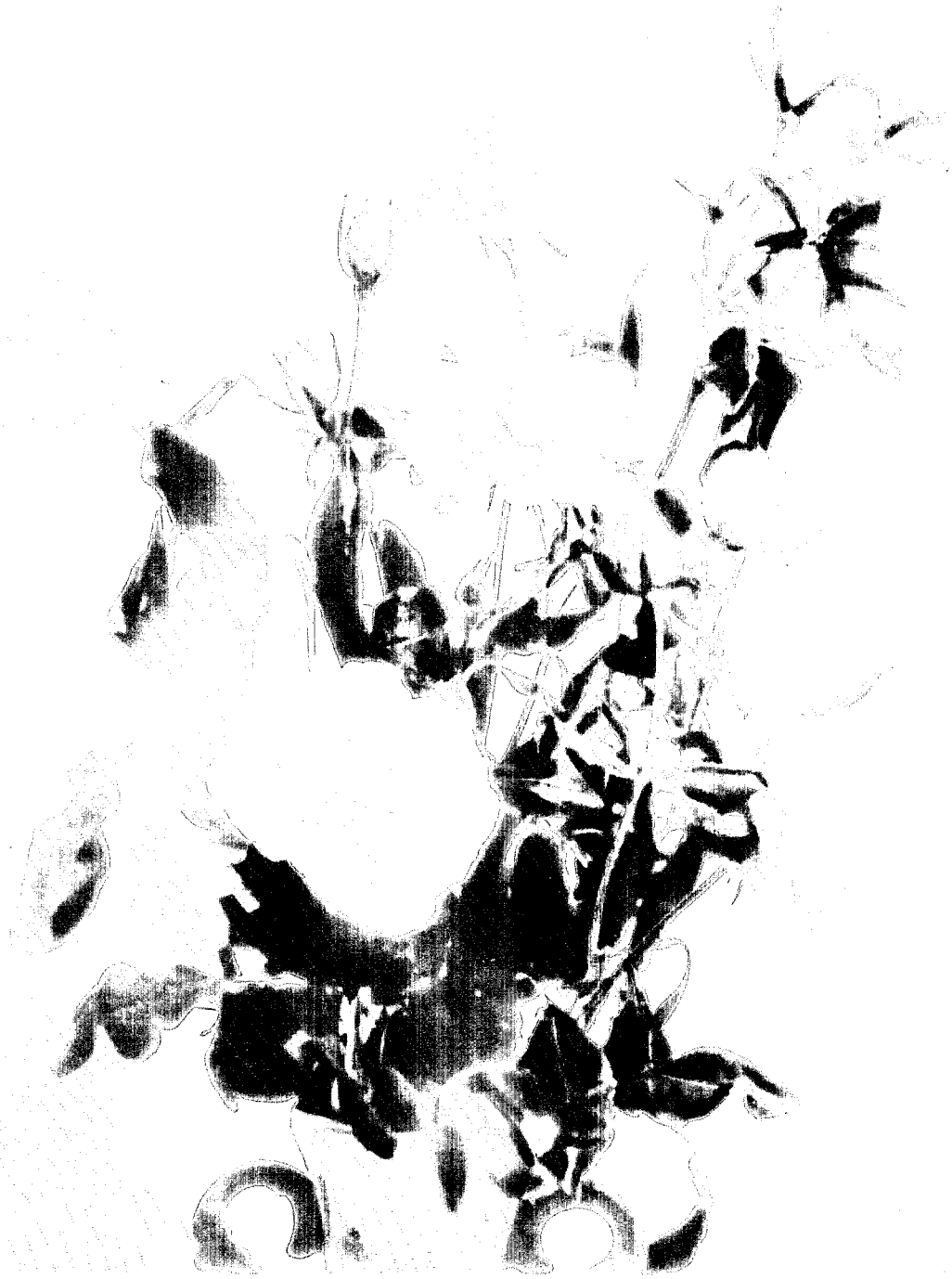
Inventor.
Paul Shamburger
By: Cobb & Cobb
Attorneys.

Patented Aug. 19, 1952

Plant Pat. 1,121

UNITED STATES PATENT OFFICE 1,121

ROSE PLANT

Paul Shamburger, Tyler, Tex.

Application February 19, 1951, Serial No. 211,616

1 Claim. (Cl. 47—61)

The present invention relates to a new and distinct variety of rose plant, originated as a sport of the variety "Floradora" (unpatented), and dominantly distinguished therefrom by the distinctive pink color of its blooms. The new variety was discovered in a cultivated nursery row of "Floradora" plants growing on my nursery property near Tyler, in Smith County, Texas.

The parent variety is a bush rose of the polyantha class, and is notable for the imbricated arrangement of the petals of its flowers, by the long-lasting habit of the flowers both on the bush and as cut-flowers, and by their unique scarlet color effect which is maintained to an extraordinary degree throughout the blooming season.

Of primary importance here, however, is the distinctly different, pink color of the flowers of the new variety. Aside from this color difference, the new variety is generally similar to its parent "Floradora" except for minor differences in its foliage, thorns and habit of growth which do not detract from the desirable and attractive qualities of the combination as a whole which are unique in a pink rose.

Asexual reproduction of the new variety by budding at Tyler, Texas, shows that the foregoing characteristics come true to form and are established and transmitted through succeeding propagations.

The accompanying drawing shows specimens of the flowers and foliage of the new variety in different stages of development.

The following is a detailed description of the new variety, with color terminology in accordance with Ridgway's Color Standards and Nomenclature, except where general color terms of ordinary dictionary significance are obvious:

Type: Hardy; bush; outdoor; sport; for cut-flowers and garden decoration.
Class: Hybrid polyantha.
Parentage: Sport of "Floradora."
Propagation: Holds its distinguishing characteristics through succeeding propagations by budding, which is the only method tried to date.

*Flower*

Locality where grown and observed: Tyler, Texas.
Flowers borne: Singly or several to stem; in irregular cluster; on medium length stems.
Quantity of bloom: Free, outdoors.
Continuity: Continuous.
Fragrance: Slight; nutty.

Bud:
*Peduncle.*—Medium length; medium heavy; erect; reddish; smooth.
*Before calyx breaks.*—Size—medium. Form—pointed; without foliaceous appendages on the surface and without foliaceous parts extending beyond the tip of the bud. Color—Deep Dull Yellow-Green, Plate XXXII, 33'', K.
*As calyx breaks.*—Color—Deep Dull Yellow-Green, Plate XXXII, 33'', K.
*As first petal opens.*—Size—medium. Form—globular. Color—Eosine Pink, Plate I, 1, *d*. Opening—opens up well.

Bloom:
*Size, when fully open.*—Medium; 2½ inches to 3 inches.
*Petalage.*—Very double; from 35 to 40 petals; arranged irregularly.
*Form.*—Cupped at first; becoming flat-cupped; becoming later, at maturity, loosely flat-cupped.

Petals: Medium to thick; soft; with inside and outside satiny.
*Shape.*—Outside—ovate. Intermediate—ovate; scalloped with one notch. Inside—ovate; scalloped irregularly with one notch.

This description of a newly opened flower was made from a rose grown outdoors, in the month of October, 1950, at Tyler, Texas:

*Color.*—Outside petal—outside surface: Shrimp Pink, Plate I, 5, *f*; inside surface—Shrimp Pink, Plate I, 5, *f*. Intermediate petal—outside surface: La France Pink, Plate I, 3, *f*; inside surface: La France Pink, Plate I, 3, *f*. Inner petal—outside surface: Eosine Pink, Plate I, 1, *d*; inside surface: Eosine Pink, Plate I, 1, *d*.
*Behavior.*—Drop off cleanly; fading brown, especially in hot weather.
*Flower longevity.*—On bush in garden—5 days in October; cut roses grown outdoors, kept at living room temperatures—4 days in October.

*Reproductive organs*

Stamens: Medium number; irregularly mixed with petaloids; Yellow.
Filaments: Medium length; Yellow; most with anthers.
Anthers: Medium size; Yellow; open at various times.
Pollen: Sparse; Yellow.

Pistils: Medium number.
Styles: Uneven; medium length; medium heavy; bunched.
Stigma: Yellow.
Ovaries: Enclosed in calyx.
Hips: Short; globular; Green; very smooth; walls thick and fleshy.
Sepals: Moderate length; curled.
Seeds: Very few; small.

*Plant*

Foliage:

*Leaves.*—Compound of five leaflets; normal abundance; medium size; soft; glossy.

*Leaflets.*—Shape—ovoid with apex acute; base acute; margin serrate.

*Color.*—Mature—upper surface: Dark Dull Yellow-Green, Plate XXXII, 31, *m*; under surface: Deep Dull Yellow-Green, Plate XXXII, 31, *k*. Young—upper surface: Liver Brown, Plate XIV, 7, *m*; under surface: Liver Brown, Plate XIV, 7, *m*.

*Rachis.*—Medium heavy. Upper side and under side—smooth.

*Stipules.*—Moderately long; medium width; with points of medium length turning out at an angle of less than 90°.

*Disease.*—Resistant to mildew and blackspot.

Growth:

*Habit.*—Bushy; upright.

*Growth.*—Free.

*Canes.*—Medium heavy.

*Main stems.*—Bright green. Thorns—few; medium length; hooked downward; with short, broad base. Prickles and hairs—none.

*Branches.*—Bright green. Thorns—few; medium length; hooked downward; with short, broad base. Prickles and hairs—none.

*New shoots.*—Green-bronze. Thorns—very few; medium length; hooked downward; with short, broad base. Prickles and hairs—none.

I claim:

A new and distinct variety of rose plant, characterized as to novelty by its general similarity to its parent "Floradora" (unpatented), but dominantly distinguished therefrom by the distinctive pink color of its flowers, substantially as herein shown and described.

PAUL SHAMBURGER.

No references cited.